United States Patent [19]

McIntyre

[11] 4,014,333

[45] Mar. 29, 1977

[54] INSTRUMENT FOR ASPIRATING AND IRRIGATING DURING OPHTHALMIC SURGERY

[76] Inventor: David J. McIntyre, 20245 Redmond-Fall-City Road, Redmond, Wash. 98052

[22] Filed: Sept. 22, 1975

[21] Appl. No.: 615,216

[52] U.S. Cl. .............................. 128/240; 128/214.4; 128/276
[51] Int. Cl.² .......................................... A61M 3/00
[58] Field of Search .......... 128/240, 241, 230, 276, 128/277, 278, 2 A, 214.4; 32/57, 40

[56] References Cited

UNITED STATES PATENTS

| | | | |
|---|---|---|---|
| 2,564,977 | 8/1951 | Hsi Hu | 128/276 X |
| 3,757,771 | 9/1973 | Ruegg et al. | 128/214.4 |
| 3,766,916 | 10/1973 | Moorehead et al. | 128/214.4 |
| 3,774,604 | 11/1973 | Danielsson | 128/214.4 |
| 3,807,048 | 4/1974 | Malmin | 32/57 X |
| 3,810,471 | 5/1974 | Truhan | 128/276 |
| 3,812,855 | 5/1974 | Banko | 128/276 |
| 3,875,938 | 4/1975 | Mellor | 128/214.4 |
| 3,902,495 | 9/1975 | Weiss et al. | 128/276 |

*Primary Examiner*—John D. Yasko
*Attorney, Agent, or Firm*—Christensen, O'Connor, Garrison & Havelka

[57] ABSTRACT

Disclosed is an instrument useful for effecting aspiration and irrigation during ophthalmic surgery. The disclosed embodiment comprises two, telescopically disposed cannulae and a connector which couples the two cannuli and forms fluid-tight seals with each. Each cannula consists of a rigid, small-diameter tube and a Luer hub (or "mount") coaxial therewith. The tube of the inner cannula is telescopically disposed within the outer cannula, the diameters of the cannulae being such that a passage is defined therebetween. The connector is of one-piece, rigid construction and includes a generally cylindrical body having a first nipple extending axially from one of its ends and a second nipple extending radially from one side. The first nipple is frictionally engaged within and forms a fluid-tight seal with the hub of the outer cannula. A cavity extends from the end of the first nipple through the body of the connector and terminates at the end of the body remote from the nipple. The tube of the inner cannula extends through the cavity and the hub and tube of the outer cannula. A portion of the connector body defining the mentioned cavity forms a fluid-tight seal with the exterior of the tube of the inner cannula. A passage extends from the cavity in the connector to the tip of the second nipple. The second nipple is coupled to a tubing via which irrigating fluid can be supplied to the instrument. In use, irrigating fluid is transmitted via the passage through the second nipple to the cavity and thence through the passage defined between the inner and outer cannulae. The hub of the inner cannula is connected to a syringe by which a vacuum can be applied to the passage defined by the inner cannula to effect aspiration of fluid from the surgical site through the inner cannula.

15 Claims, 8 Drawing Figures

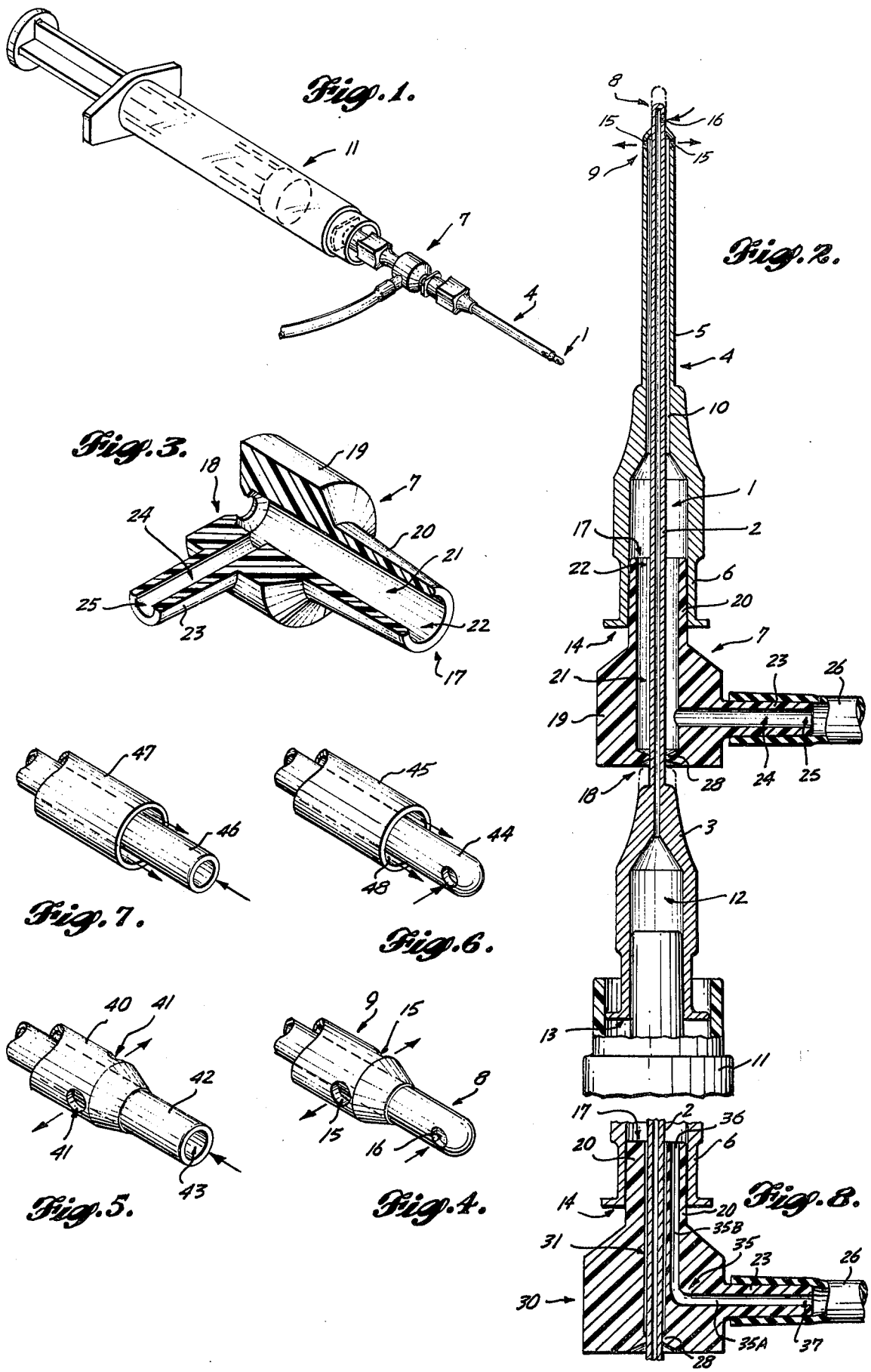

INSTRUMENT FOR ASPIRATING AND IRRIGATING DURING OPHTHALMIC SURGERY

BACKGROUND OF THE INVENTION

This invention relates to instruments for effecting aspiration and irrigation during ophthalmic surgery.

Numerous aspiration-irrigation systems useful in ophthalmic surgery have been proposed. The mechanically powered systems thus far introduced are generally quite expensive and have a number of disadvantages. Several manual systems have been in limited use. Among these are the Fuch's two-way syringe (see *Am. J. Ophthal.*, 3:1264–0,1971) and the Fink-Weinstein two-way syringe (see *Am. J. Ophthal.*, 58:129–30, 1964). These are manual pumping systems with double-lumen cannulae attached. They allow the surgeon to manually pump fluid from the irrigation system to the aspiration system with the resultant pickup of dissolved or dispersed material. The O'Gawa syringe (see *Am. J. Ophthal.*, 64:970, 1967) has two separate and parallel lumen, thus allowing aspiration and irrigation through separate channels. It was designed for syringe aspiration by a surgical assistant who is necessarily remote from the operating field. Its major disadvantage is the difficulty of precise aspiration control inherent in the time lag between the surgeon and his assistant. Generally speaking, the manual systems proposed to date are rather complex in their design and manufacture and somewhat cumbersome to use, disassemble, clean, sterilize and reassemble.

It is an object of the present invention to provide a compact, uncomplicated instrument for effecting aspiration and irrigation during ophthalmic surgery that is simple to operate, disassemble, clean, sterilize and reassemble and inexpensive to manufacture. It is a further object to provide such an instrument having two telescopically disposed cannulae, each of which can be quickly and easily separated from the other (and from the remainder of the instrument) and quickly and easily replaced by another cannula having, for example, a different tip configuration or bore size. It is a further object to provide an instrument of the type described in which the cannulae define separate, substantially concentric passages for supplying fluid to and withdrawing fluid from the surgical site.

SUMMARY OF THE INVENTION

In summary, this invention is directed to an instrument for effecting aspiration and irrigation during ophthalmic surgery. The instrument is particularly suited for aspiration and irrigation of cataractous lens cortex during extra-capsular cataract extraction. The instrument comprises an elongated inner cannula telescopically disposed within a shorter outer cannula, the cannulae being rigid and substantially coaxial and defining a first passage therebetween. Each cannula has an insertable end adjacent to the insertable end of the other. Preferably, each cannula is comprised of a small diameter, hollow tube defining the insertable end of the cannula and a larger diameter, hollow, open-ended hub (or mount) coaxial with the tube, the hub of the inner cannula being connectable to a push-pull type syringe and the hub of the outer cannula being engageable with a connector which interconnects the two cannulae.

The passage between the two cannulae extends from the insertable end of the outer cannula to the remote end of the outer cannula remote from its insertable end. The inner cannula defines a second passage extending from its insertable end to the remote end of the inner cannula remote from its insertable end. The insertable end of the outer cannula has an exterior orifice communicating with the passage between the two cannulae and the insertable end of the inner cannula has an exterior orifice communicating with the passage that it defines.

The connector means of which the instrument is comprised interconnects and forms a fluid-tight seal with each of the cannulae at locations remote from their respective insertable ends. The connector defines an interior cavity communicating with first and second ports spaced apart on its exterior. The cavity communicates via the first port with the passage between the two cannulae at the remote end of the outer cannula. The inner cannula passes through the connector means and has its remote end accessible for connection of the second passage to a vacuum source.

This invention is also directed to a connector useful in the instruments of this invention. More particularly, the connector is useful for interconnecting in telescoped relation two cannulae of a type having a rigid, small diameter tube and a larger diameter, hollow, open-ended hub coaxial therewith. The connector comprises a rigid body (preferably composed of plastic and of one-piece construction) having first and second ends and defining a cavity extending between said ends for receiving a longitudinal segment of the tube of a cannula of the mentioned type. The body further defines a passage communicating with a first port at the first end of the body and including a second port located on the exterior of the body at a location remote from the first end of the body. The body also includes at its first end means for coupling it to the hub of the outer cannula so as to place the passage between the two cannulae in communication with the first port. Preferably, the means for coupling the connector to the outer cannula is a tapered nipple insertable into and sealingly engageable with the hub of the outer cannula. Also, the first port and the end of the cavity at the first end of the body are preferably coincident, the passage communicating with the port via said cavity.

BRIEF DESCRIPTION OF THE DRAWINGS

FIG. 1 is an isometric view of an aspiration-irrigation instrument according to the present invention.

FIG. 2 is an enlarged longitudinal cross section view of the instrument of FIG. 1.

FIG. 3 is a cross-sectional view of a cannulae connector of this invention which is embodied in the instrument of FIGS. 1 and 2.

FIG. 4 is an enlarged isometric view of the insertable ends of the cannulae of the instrument of FIGS. 1–3.

FIG. 5–7 are isometric views of alternative configurations of the insertable ends of the cannulae of the instruments of the invention.

FIG. 8 is a cross-sectional view of another cannulae connector of this invention embodied in an instrument otherwise identical to that shown in FIGS. 1–4.

DETAILED DESCRIPTION OF THE INVENTION AND PREFERRED EMBODIMENTS

Referring to FIGS. 1–4 of the drawings, there are shown the presently preferred embodiments of the aspiration-irrigation instruments and cannulae connectors of the present invention. As indicated previously the instrument is especially useful for effecting aspiration of cortical lens material during extra-capsular cataract extraction. The embodiment shown is comprised of an inner cannula 1 consisting of a small diameter, hollow tube 2 and a larger diameter, hollow, open-ended hub 3 connected coaxially to one end of the tube 2. The hub 3 is typical of the type used on hypodermic needles and is commonly referred to as a "Luer hub" or Luer mount." The instrument is further comprised of an outer cannula 4, which like the inner cannula, consists of a small diameter, hollow tube 5 and a larger diameter, hollow, open-ended hub 6 connected coaxially thereto.

Interconnecting the two cannulae is a connector 7 (described in detail below) through which the tube 2 of the inner cannula 1 extends. Each cannula 1,4 has an insertable end 8,9 adjacent to the insertable end of the other. The external diameter of the tube 2 of the inner cannula 1 and the internal diameter of the tube 5 and hub 6 of the outer cannula 4 are such that the two cannulae define a passage 10 therebetween.

The hub 3 of the inner cannula is coupled with a conventional syringe 11 for drawing a vacuum on a passage 12 extending through the inner cannula from its insertable end 8 to its remote end 13. The passage 10 between the cannulae extends from the insertable end 9 of the outer cannula 4 to the remote end 14 of the outer cannula. The passage 10 between the cannulae and the passage 12 through the inner cannula are sometimes referred to herein as the "irrigation passage" and the "aspiration passage," respectively.

The insertable end of the outer cannula has two exterior orifices 15 communicating with the irrigation passage 10 and the insertable end of the inner cannula has a single exterior orifice 16 communicating with the aspiration passage 12. The arrows associated with orifices 15 and 16 indicate the directions of fluid flow during normal operation of the instrument explained fully hereinafter.

The cannulae can be inexpensively manufactured from unsharpened, conventional stainless steel hypodermic needles by a cold forming operation involving spinning the needle while pressing its tip into a suitably shaped tungsten carbide or hardened steel mold, polishing the formed tip with jeweler's rouge and drilling the orifices by electrical discharge machining.

As best seen by reference to FIG. 3, the connector 7 consists of a one-piece, rigid plastic body having first and second ends 17,18 and including a generally cylindrical segment 19, which is substantially coaxial with the cannulae. ("Delrin," an acetal resin available from E. I. Du Pont de Nemours & Company has been found to be an acceptable plastic for manufacture of the connector. Numerous other plastics can also be used.) The first end of the body is defined by a hollow-tapered (frusto-conical) nipple 20 coaxial with the cylindrical segment of the body. In the instrument of FIG. 2, the exterior of this nipple 20 is frictionally engaged with and forms a fluid-tight seal circumferentially of the interior of the hub 6 of the outer cannula 4.

It will be noted that the body defines a cavity 21 extending between its ends and includes a first port 22 at the first end via which the cavity 21 communicates with the irrigation passage 10. The cavity is generally cylindrical, is coaxial with the cannulae, and accomodates a longitudinal segment of the tube 2 of the inner cannula 1. Near the second end of the connector 18, a segment 28 of the cavity 21 has a circular cross section of a diameter substantially equal to the external diameter of the inner cannula tube 2. The portion of the connector defining this constricted segment of the cavity forms a fluid-tight seal circumferentially of the exterior of the inner cannula tube. From this constricted segment to the first end of the connector, the cavity is of substantially larger diameter of the inner cannula tube. (As subsequently explained, irrigation fluid is tranmitted through this latter segment of cavity to the first port 22.) From the constricted segment of the cavity toward the second end of the connector, the cavity flares outwardly such that there is a conical recess at the second end serving as a guide for the tip of the tube of the inner cannula during its insertion through the connector.

As depicted by the dashed lines in FIG. 2, the inner cannula tube 2 is reciprocably slidable through the connector and through the outer cannula such that the relative positions of the insertable ends of the cannulae can be varied to meet the needs and desires of the surgeon.

Extending radially from the cylindrical segment 19 of the connector 7 is a second hollow, tapered (frusto-conical) nipple 23. Extending axially through the second nipple and radially through the cylindrical segment of the body is a passage 24 which includes a second connector port 25 at the tip of nipple 23. This passage 24 intersects the cavity 21 in the body and is thus in communication with the first connector port 22 via the cavity. Fitted on the second nipple 23 is a length of flexible plastic tubing 26 via which irrigating fluid can be supplied to the instrument. The source of irrigating fluid may be, for example, a bottle of saline solution elevated to a level that will provide the rate of fluid flow desired by the surgeon utilizing the instrument. Alternatively, the tubing may be connected to a liquid-filled syringe which can be operated by the surgeon or his assistant.

Referring now to FIG. 8, there is shown another embodiment of the cannulae connector of the present invention. It is similar to the connector shown in FIGS. 1–4 and elements and features that have identical counterparts in the embodiment of FIGS. 1–4 are simply identified by the same reference numerals without further discussion. In the embodiment of FIG. 8, the connector 30 defines a cavity 31 that accomodates a longitudinal segment of the tube 2 of the inner cannula. As in the embodiment of FIGS. 1–4, the cavity has a constricted segment 28 near the second end of the connector and the portion of the connector defining this segment has a circular cross section substantially equal to and forming a fluid-tight seal with the exterior of the inner cannula tube. As will be evident from FIG. 8, cavity 31 does not serve as a passage for irrigating fluid. Therefore, between the constricted segment 28 and the first end of the connector 17 the cavity is made just slightly larger than the tube of the inner cannula so that the tube can be easily inserted through and removed from the connector. The connector also defines a passage of cavity 35, one segment of which 35A extends axially through the second nipple 23 on the connector, and radially through the cylindrical segment 19 of the connector, and a second segment 35B of which parallels the cavity. The passage 35 includes a first port 36 at the tip of the first nipple 20 and a second port 37 at the tip of the second nipple 23. It will be evident that the instrument of FIG. 8 functions in the same manner as that of FIGS. 1–4.

In the embodiment of FIG. 5, the outer cannula 40 has two orifices 41 and is configured the same as outer cannula shown in FIG. 4. The inner cannula 42, on the other hand, has an orifice 43 in its axial end instead of an orifice opening to the side. In the embodiment of FIG. 6, the inner cannula 44 is configured the same as that in the embodiment of FIG. 4. The outer cannula 45 however has no side orifice, but rather has an orifice 48 in its axial end which communicates with the passage between the cannulae. In the embodiment of FIG. 7, the inner cannula 46 is configured like the inner cannula 42 of the embodiment of FIG. 5 and the outer cannula 47 is configured like that of the embodiment shown in FIG. 6. Although the tubes of the two cannulae in the embodiments of FIGS. 6 and 7 are shown to be exactly coaxial, this is not essential, and in practice the tubes of the cannulae may even be touching due to one or both tubes not being exactly straight. The arrows in FIGS. 5–7 show the direction of flow of fluid to and from the orifices in the cannulae.

The tube of inner cannula used in the instruments of this invention will normally be of a gauge ranging from 21 (I.D. = 0.020 in.; O.D. = 0.032 in.) to 26 (I.D. = 0.009 in.; O.D. = 0.018 in.), with gauges from 23 (I.D. = 0.012 in.; O.D. = 0.025 in.) to 25 (I.D. = 0.010 in.; O.D. = 0.020 in.) being preferred. The tube of the outer cannula will normally be of a gauge from 18 (I.D. = 0.033 in.; O.D. = 0.050 in.) to 21 (I.D. = 0.020 in.; O.D. = 0.032 in.). Typically, the outer cannula will be three or four gauges larger than the inner cannula. I prefer that the cross-sectional area of the irrigation passage be about 3½ times that of the aspiration passage to assure an adequate flow of liquid to the surgical site.

Syringes used in the instruments of this invention typically will have capacities ranging from 2 to 20 ml. or larger. I prefer a syringe having a capacity of 10 ml.

Althrough the instruments and the cannulae connectors of the present invention have been described by reference to the presently preferred embodiments, it will be evident that various modifications can be made in those embodiments without departing from the spirit and scope of the present invention. For example, the outer cannula could be an extension of the connector rather than being a separate element. Similarly, the hubs of the cannulae could be replaced by other means of coupling the cannulae to the connector and to the source of vacuum. Also, the second nipple on the connector could be eliminated and the end of the tubing through which irrigating fluid is supplied could be adhesively bonded in a suitable recess in the cylindrical segment of the connector.

As will be apparent from the foregoing, the preferred embodiments of the instruments of this invention can be economically manufactured, quickly assembled and quickly disassembled for cleaning and sterilization. The ease of assembly and disassembly allows selection and interchangability among a group of cannulae having various dimensions and tip configurations. Also, the relative position of the ports in the insertable end portions of the cannulae can be changed almost instantaneously during use of the instrument. The connector of the present invention lends itself to being economically manufactured and supplied (with or without a tubing attached) as a pre-sterilized disposable component of the instrument.

What is claimed is:

1. An instrument for effecting aspiration and irrigation during ophthalmic surgery comprising:
an elongated inner cannula telescopically disposed within a shorter outer cannula, the cannulae being rigid and substantially coaxial and defining a first passage therebetween, each cannula having an insertable end adjacent to the insertable end of the other, the first passage extending from the insertable end of the outer cannula to the remote end of the outer cannula remote from its insertable end, the inner cannula defining a second passage extending from its insertable end to the remote end of the inner cannula remote from its insertable end, the insertable end of the outer cannula having an exterior orifice communicating with the first passage, the insertable end of the inner cannula having an exterior orifice communicating with the second passage; and connector means interconnecting and forming a fluid-tight seal with each of the cannulae at locations remote from their insertable ends, the connector means having an interior cavity communicating with first and second ports spaced apart on its exterior, the cavity communicating via the first port with the first passage at the remote end of the outer cannula, the second port being accessible for connection to a source of liquid, and the inner cannula passing through the connector means and having its remote end accessible for connection of the second passage to a vacuum source.

2. The instrument of claim 1 wherein the outer cannula comprises a first, small diameter, hollow tube defining the insertable end of the outer cannula and a first, larger diameter, hollow, open-ended hub coaxial with the first tube, the first hub defining the remote end of the outer cannula, and wherein the connector means is frictionally engaged with and forms a fluid-tight seal with the interior of the first hub.

3. The instrument of claim 2, wherein the inner cannula comprises a second hollow tube defining the insertable end of the inner cannula and a second hollow, open-ended hub coaxial with the first hub, the second hub defining the remote end of the inner cannula, and wherein the connector means forms a fluid-tight seal circumferentially of the exterior of the second tube.

4. The instrument of claim 3 further comprising a syringe operatively connected to the hub of the inner cannula.

5. The instrument of claim 3, wherein the second tube is reciprocally slidable through the connector means and through the outer cannula thereby to vary the relative positions of the insertable ends of the cannulae.

6. The instrument of claim 2, wherein the connector means comprises a generally cylindrical body defining the cavity, the body having first and second axial ends, and a first frusto-conical nipple at its first end, the nipple defining the first port.

7. The instrument of claim 6, wherein the body includes a second frusto-conical nipple extending substantially radially from the body, the second nipple defining the second port.

8. The instrument of claim 1 wherein the inner cannula extends through the cavity in the connector means.

9. The instrument of claim 1, wherein the inner cannula is reciprocally slidable through the connector means and through the outer cannula thereby to vary the relative positions of the insertable ends of the cannulae.

10. The instrument of claim 1 further comprising a syringe operatively connected to the remote end of the inner cannula.

11. The instrument of claim 1 wherein the connector means comprises a rigid body having first and second ends and defining the cavity, the cavity extending between the ends of the body, the inner cannula extending through the cavity, a portion of the body defining the cavity forming a fluid-tight seal with the exterior of the inner cannula.

12. The instrument of claim 11 wherein the diameter of the cavity is substantially larger than the diameter of the inner cannula and wherein the first port is coincident with the end of the cavity at the first end of the body and wherein the body further defines a passage extending between the second port and the cavity.

13. A connector for coupling in telescoped relationship a first cannula having a small diameter and a second cannula having a larger diameter, hollow, open ended hub coaxial with said first cannula, said first cannula and the hub of said second cannula defining an annularly shaped passage therebetween, said connector comprising:

a unitary rigid body having a first end and a second end, said body adjacent its first end being tapered for insertion into and sealing engagement with said hub, said body defining a cavity between said first and second ends for receiving a longitudinal segment of said first cannula when said body is engaging said hub, said cavity being sized to receive said first cannula in sealing engagement adjacent said second end, said body further defining a passage communicating between a first port on the exterior of said body displaced from said first end and a second portion positioned on said first end to communicate with said annular passage when said body is engaging said hub, said first cannula when positioned in said cavity forming a first fluid flow channel and said passage in said body forming a second fluid flow channel independent from said first channel when said first cannula is positioned in said cavity.

14. The connector of claim 13 wherein said cavity extends through said body from said first end to said second end, said cavity terminating at said first end in an opening corresponding to said second port, said second port having a diameter larger than the transverse section of said first cannula, said passage communicating with said second port through said cavity.

15. The connector of claim 14 wherein said cavity is cylindrically shaped and located to receive said first cannula in coaxial relationship and sized to define an annular region surrounding said first cannula and an annular second port on said first end when said body is engaging said hub and said first cannula is positioned in said cavity.

* * * * *